United States Patent [19]

Albers-Schonberg et al.

[11] 4,310,519
[45] Jan. 12, 1982

[54] NOVEL SUBSTANCES AND PROCESS FOR THEIR PRODUCTION

[75] Inventors: George Albers-Schonberg, Princeton; Hyman Wallick, Springfield; Robert E. Ormond, Edison; Thomas W. Miller, Carteret; Richard W. Burg, Murray Hill, all of N.J.

[73] Assignee: Merck & Co., Inc., Rahway, N.J.

[21] Appl. No.: 940,682

[22] Filed: Sep. 8, 1978

Related U.S. Application Data

[63] Continuation-in-part of Ser. No. 874,607, Feb. 2, 1978, abandoned, which is a continuation-in-part of Ser. No. 772,601, Mar. 2, 1977, abandoned, which is a continuation-in-part of Ser. No. 678,328, Apr. 19, 1976, abandoned.

[51] Int. Cl.$^3$ ..................... A61K 31/71; C07H 17/08
[52] U.S. Cl. ..................... 424/181; 435/76; 435/119; 435/253; 260/343.41; 536/17 R
[58] Field of Search ............ 424/180, 181; 536/17 R, 536/17 C

[56] References Cited

U.S. PATENT DOCUMENTS

| | | | |
|---|---|---|---|
| 3,950,360 | 4/1976 | Aoki et al. | 260/343.2 R |
| 4,134,973 | 1/1979 | Fisher et al. | 536/17 R |
| 4,160,083 | 7/1979 | Cole | 536/17 R |
| 4,160,084 | 7/1979 | Miller et al. | 536/17 R |
| 4,160,861 | 7/1979 | Cole et al. | 536/17 R |
| 4,161,583 | 7/1979 | Wilson et al. | 536/17 R |

OTHER PUBLICATIONS

Mishima et al., "Tetrahedron Letters", vol. 10, pp. 711-714, 1975.
Derwent Abstract 76268w/46 to Sankyo Co. Ltd.

*Primary Examiner*—Johnnie R. Brown
*Attorney, Agent, or Firm*—David L. Rose; Harry E. Westlake

[57] ABSTRACT

Novel compounds are produced by the fermentation of a nutrient medium with the previously undescribed microorganism *Streptomyces avermitilis*. They may be isolated by solvent extraction and chromatographic fractionation techniques. The compounds, which are described generically as C-076 have significant parasiticidal activity. The compounds may be included in compositions for the oral or parenteral administration to animals for the treatment of parasitic infections.

14 Claims, 8 Drawing Figures

NOVEL SUBSTANCES AND PROCESS FOR THEIR PRODUCTION

CROSS REFERENCE TO RELATED APPLICATIONS

This application is a continuation-in-part of our co-pending application Ser. No. 874,607 filed Feb. 2, 1978, now abandoned; which is a continuation-in-part of our application Ser. No. 772,601, now abandoned, filed Mar. 2, 1977, which is a continuation-in-part of application Ser. No. 678,328 filed Apr. 19, 1976, now abandoned.

SUMMARY OF THE INVENTION

This invention is concerned with novel chemical compounds. In particular, it is concerned with novel compounds, collectively identified as C-076, which are produced by the fermentation of a nutrient medium with a strain of the microorganism *Streptomyces avermitilis*. Thus, it is an object of this invention to provide compounds described generically as C-076 and a method for preparing such products. It is a further object to provide novel compounds. It is a further object of this invention to provide a method for the recovery and purification of such compounds. These substances have significant and broad spectrum antiparasitic activity and it is thus an additional object of this invention to provide novel anti-parasitic compositions containing one or more of the C-076 compounds. Further objects of this invention will become apparent from the following description of this invention.

DESCRIPTION OF THE INVENTION

In accordance with this invention, a class of substances described generically herein as C-076, is prepared by growing under controlled conditions, previously undescribed strains of microorganisms. At least eight distinct but closely related novel compounds are produced by *Streptomyces avermitilis*. They are described herein as C-076 A1a, A1b, A2a, A2b, B1a, B1b, B2a, and B2b. All have significant antiparasitic activity. They may be obtained by fermentation and recovered in substantially pure form as described herein.

Based on taxonomic studies, the microorganisms capable of producing these C-076 compounds are of a new species of the genus Streptomyces, which has been named *Streptomyces avermitilis*. One such culture, isolated from soil is designated MA-4680 in the culture collection of Merck & Co., Inc., Rahway, N.J. A C-076 producing sample of this culture has been deposited in the permanent culture collection of the Fermentation Section of the Northern Utilization Research Branch, U.S. Department of Agriculture at Peoria, Ill., and has been assigned the accession number NRRL 8165. A sample of NRRL 8165 has also been deposited, without restriction as to availability, in the permanent culture collection of the American Type Culture Collection at 12301 Parklawn Drive, Rockville, Md. 20852, and has been assigned the accession number ATCC 31,267.

The morphological and cultural characteristics of *Streptomyces avermitilis* are set forth below: Morphology; Sporophores form spirals as side branches on aerial mycelia. Spirals are compact but become more open as culture ages. Spores are in chains of more than 15 spores and are usually spherical to oval at 970× magnification. Sporulation is observed on oatmeal agar, glycerol-asparagine agar, salts-starch agar and egg albumin agar. Spore surface is smooth as seen by electron microscopy.

Oatmeal agar

Vegatative growth: Reverse—very dark brown
Aerial mycelium: Powdery, brownish gray (41i)* mixed with white.
Soluble pigment: Brown

Czapek Dox agar (sucrose nitrate agar)

Vegetative growth: Poor, colorless
Aerial mycelium: Scant, grayish
Soluble pigment: Light grayish tan

Egg albumin agar

Vegetative growth: Tan
Aerial mycelium: Moderate, light grayish-yellow-brown (3ge)* mixed with white.
Soluble pigment: Light yellowish tan

Glycerol asparagine agar

Vegetative growth: Reverse—yellowish brown
Aerial mycelium: Powdery, brownish gray (41i)* mixed with white.
Soluble pigment: Light, yellowish brown

Inorganic salts-starch agar

Vegetative growth: Reverse—grayish yellowish brown.
Aerial mycelium: Powdery, light brownish gray (4ig)* edged with darker brownish gray (41i)*.
Soluble pigment: Light yellowish brown

Yeast extract-dextrose+salts agar

Vegetative growth: Reverse—dark brown
Aerial mycelium: Moderate, brownish white
Soluble pigment: Brown

Yeast extract-malt extract agar

Vegetative growth: Reverse—dark brown
Aerial mycelium: Moderate, brownish white
Soluble pigment: Brown

Peptone-iron-yeast extract agar

Vegetative growth: Dark brown
Aerial mycelium: None
Soluble pigment: Dark brown to black
Melanin: Positive
H S production: Positive

Nutrient agar

Vegetative growth: Tan
Aerial mycelium: Sparse, grayish
Soluble pigment: Light brown

Nutrient starch agar

Vegetative growth: Tan
Aerial mycelium: Sparse, grayish white
Soluble pigment: Light brown
Hydrolysis of starch: Good

Potato plug

Vegetative growth: Tan
Aerial mycelium: Brown mixed with grayish white
Soluble pigment: Grayish brown

Loeffler's Blood serum

Vegetative growth: Grayish tan

Aerial mycelium: None
Soluble pigment: Some browning of medium
Liquefaction: None

Nutrient tyrosine agar

Vegetative growth: Reverse—dark brown to black
Aerial mycelium: Sparse, grayish
Soluble pigment: Dark brown
Decomposition of tyrosine: None

Carbon utilization

Pridham-Gottlieb basal medium + 1% carbon source;
+ = growth; no growth as compared to negative control (no carbon source).

| | | |
|---|---|---|
| Glucose | + | |
| Arabinose | + | |
| Cellulose | − | |
| Fructose | + | |
| Inositol | + | |
| Lactose | + | |
| Maltose | + | |
| Mannitol | + | |
| Mannose | + | |
| Raffinose | + | |
| Rhamnose | + | |
| Sucrose | + | |
| Xylose | + | |

Nutrient gelatin agar

Vegetable growth: Tan
Aerial mycelium: Sparse, grayish white
Soluble pigment: Light brown
Liquefaction of gelatin: Good

Gelatin stabs

Vegetative growth: Brown ring
Aerial mycelium: None
Soluble pigment: Greenish brown
Liquefaction of gelatin: Complete

Skim milk agar

Vegetative growth: Dark brown
Aerial mycelium: None
Soluble pigment: Dark brown
Hydrolysis of casein: Good

Litmus milk

Vegetative growth: Dark brown growth ring
Aerial mycelium: None
Color: Dark brown Coagulation and/or peptonization: Complete peptonization; becoming alkaline (pH 8.1).

Skim milk

Vegetative growth: Dark brown growth ring
Aerial mycelium: None
Soluble pigment: Dark brown
Coagulation and/or peptonization: Complete peptonization; becoming alkaline (pH 8.0).

Temperature range: (Yeast extract-dextrose + salts agar)

28° C.—Good vegetative growth and aerial mycelia
37° C.—Good vegetative growth and aerial mycelia
50° C.—No growth Oxygen requirement: (Stab culture in yeast extract-dextrose + salts agar)

Aerobic All readings taken after three weeks at 28° C. unless noted otherwise. pH of all media approximately neutral (6.8–7.2)

(*) Color number designations taken from Color Harmony Manual, 1958, 4th Edition Container Corporation of America, Chicago, Ill.

A careful comparison of the foregoing data with published descriptions including Bergey's Manual of Determinative Bacteriology (Eighth Edition) of known microorganisms reveals significant differences that indicate that the instant microorganism should be classified as a new species. On this basis, it was designated *Streptomyces avermitilis*.

The aboe description is illustrative of a strain of *Streptomyces avermitilis* which can be employed in the production of the C-076 compounds described herein. However, the present invention also embraces mutants of the above described microorganism. For example, those C-076 producing mutants which are obtained by natural selection or those produced by mutating agents including X-ray irradiation, ultraviolet irradiation, nitrogen mustard or like treatments are also included within the ambit of this invention.

One example of such an organism is a strain of *Streptomyces avermitilis* MA 4848 which was isolated after irradiation with ultraviolet light of *Streptomyces avermitilis* MA 4680. A lyophilized tube and a frozen vial of this culture has been deposited in the permanent culture collection of the American Type Culture Collection, and they have been assigned the accession numbers 31272 and 31271 respectively. Slightly higher fermentation yields of C-076 have been obtained using this frozen stock as inoculum.

The C-076 compounds are produced during the aerobic fermentation of suitable aqueous nutrient media under conditions described hereinafter, with a producing strain of *Streptomyces avermitilis*. Aqueous media such as those used for the production of many antibiotic substances are suitable for use in this process for the preparation of C-076.

Such nutrient media contain sources of carbon and nitrogen assimilable by the microorganism and generally low levels of inorganic salts. In addition, the fermentation media may contain traces of metals necessary for the growth of the microorganisms. These are usually present in sufficient concentration in the complex sources of carbon and nitrogen which may be used as nutrient sources, but can, of course, be added separately to the medium if desired.

In general, carbohydrates such as sugars, for example dextrose, sucrose, maltose, lactose, dextran, cerelose and the like, and starches are suitable sources of assimilable carbon in the nutrient media. The exact quantity of the carbon source which is utilized in the medium will depend, in part, upon the other ingredients in the medium but it is usually found that an amount of carbohydrate between about 0.5 and 5% by weight of the medium is satisfactory. These carbon sources can be used individually or several such carbon sources may be combined in the same medium.

Various nitrogen sources such as yeast hydrolysates, yeast autoysate, soybean meal, casein hydrolysates, yeast extracts, corn steep liquors, distillers solubles, cottonseed meal, meat extract and the like, are readily assimilable by *Streptomyces avermitilis* in the production of the C-076 compounds. The various sources of nitrogen can be used alone or in combination in amounts ranging from about 0.2 to 6% by weight of the medium.

Among the nutrient inorganic salts which can be incorporated in the culture media are the customary salts capable of yielding sodium, potassium, magnesium, ammonium, calcium, phosphate, sulfate, chloride, carbonate and like ions. Also included are trace metals such as cobalt, manganese, iron and the like.

It should be noted that the media described hereinbelow and in the Examples are merely illustrative of the wide variety of media which may be employed, and are not intended to be limitative.

The following are Examples of media suitable for growing strains of Streptomyces avermitilis for producing the C-076 compounds.

| Medium A | |
|---|---|
| Corn meal | 20.0 g. |
| Distiller's solubles | 10.0 g. |
| Soybean meal | 15.0 g. |
| Sodium citrate | 4.0 g. |
| $CaCl_2 2H_2O$ | 0.5 g. |
| Polyglycol P2000 | 2.5 ml. |
| $MgSO_4 . 7H_2O$ | 0.1 g. |
| $CoCl_2 . 6H_2O$ | 0.01 g. |
| $FeSO_4 . 7H_2O$ | 0.01 g. |
| Distilled water | 1000 ml. |
| pH 6.5 | |
| Medium B | |
| Soluble starch | 20.0 g. |
| Corn steep liquor | 15.0 g. |
| Cerelose | 5.0 g. |
| Soybean meal | 4.0 g. |
| $(NH_4)_2SO_4$ | 4.0 g. |
| Corn meal | 1.0 g. |
| Soybean oil | 2.5 ml. |
| $KH_2PO_4$ | 0.3 g. |
| $CaCO_3$ | 6.0 g. |
| Distilled water | 1000 ml. |
| pH 6.7 | |
| Medium C | |
| Tomato paste | 40.0 g. |
| Oat flour | 15.0 g. |
| Distilled water | 1000 ml. |
| pH 6.0 | |
| Medium D | |
| Oat flour | 20.0 g. |
| Tomato paste | 20.0 g. |
| Distilled water | 1000 ml. |
| pH 5.5 | |
| Medium E | |
| Dextrose | 10.0 g. |
| Peptone (Available from Difco Laboratories, Detroit, Michigan). | 5.0 g. |
| Yeast autolysate (Available as Ardamine pH from Yeast Products Inc., Paterson, New Jersey). | 3.0 g. |
| NaCl | 12.7 g. |
| KCl | 0.72 g. |
| $FeSO_4(NH_4)_2SO_4 . 6H_2O$ | 0.035 g. |
| $MgCl_2 . 6H_2O$ | 5.32 g. |
| $CaCl_2 . 2H_2O$ | 0.73 g. |
| Distilled water | 1000 ml. |
| pH 7.4 | |

The fermentation employing the C-076 producing microorganisms can be conducted at temperatures ranging from about 20° to about 40° C. For optimum results, it is most convenient to conduct these fermentations at a temperature in the range of from about 24° to about 30° C. Temperatures of about 27°-28° C. are most preferred. The pH of the nutrient medium suitable for producing the C-076 compounds can vary from about 5.0 to 9.0 with a preferred range of from about 6.0 to 7.5.

Small scale fermentations are conveniently carried out by placing suitable quantities of nutrient medium in a flask employing known sterile techniques, inoculating the flask with either spores or vegetative cellular growth of a C-076 producing strain of Streptomyces avermitilis, loosely stoppering the necks of the flask with cotton, and permitting the fermentation to proceed in a constant room temperature of about 28° C. on a rotary shaker for about 3 to 10 days. For larger scale work, it is preferable to conduct the fermentation in suitable tanks provided with an agitator and a means of aerating the fermentation medium. The nutrient medium is made up in the tank and after sterilization is inoculated with a suitable source of vegetative cellular growth of a C-076 producing strain of Streptomyces avermitilis. The fermentation is allowed to continue for from 1 to 8 days while agitating and/or aerating the nutrient medium at a temperature in the range of from about 24° to 37° C. The degree of aeration is dependent upon several factors such as the size of the fermentor, agitation speed and the like. Generally, the larger scale fermentations are agitated at about 95 to 150 RPM and about 2 to 20 cubic feet per minute of air.

The novel substances of this invention, which are generically referred to herein as C-076, are found primarily in the mycelium on termination of the Streptomyces avermitilis fermentation, and may be recovered and separated from one another as described below. Four major and four minor components of the C-076 as elaborated by Streptomyces avermitilis have been isolated. The eight different compounds are identified herein as C-076 A1a, A1b, A2a, A2b, B1a, B1b, B2a and B2b. The major components have been given the suffix "a" in our identification terminology and the minor components the suffix "b." The structural difference between the "a" and "b" compounds is believed to be the same for each of the four pairs.

As might be expected, even the major C-076 compounds are not produced in equal amounts by the fermentations described herein. In general, it has been found that the A1 compounds comprise about 20 to 30% by weight of the total C-076 complex produced, the A2 compounds about 1–20% and the B1 and B2 compounds each about 25–35%. The weight ratio of the "a" series of compounds to the "b" series is about 85:15 to 99:1.

The separation of the C-076 series of compounds from the whole fermentation broth and the recovery of the individual components is carried out by solvent extraction and application of chromatographic fractionations with various chromatographic techniques and solvent systems.

The C-076 compounds have slight solubility in water, but are soluble in organic solvents. This property may be conviently employed to recover them from the fermentation broth. Thus in one recovery method, the whole fermentation broth is filtered and the aqueous filtrate discarded. The wet mycelial cake is then extracted with an appropriate organic solvent. While any organic solvent may be employed, it is preferable to use a water miscible solvent such as acetone, methanol, ethanol and the like. Generally, several extractions are desirable to achieve maximum recovery. The solvent removes the C-076 active components as well as other substances lacking the antiparasitic activity of C-076. If the solvent is a water miscible one, the water is also removed from the wet mycelia. The extracted mycelia may be discarded. The solvent extracts are evaporated to remove the organic solvent and extracted several times with a second solvent. When the first extraction employs a water miscible solvent, the second extraction preferably employs a water immiscible solvent such as chloroform, methylene chloride, carbon tetrachloride, ethylacetate, methylethyl ketone, methylisobutyl ketone and the like. These latter extracts are dried and concentrated using known techniques to afford a residue comprising C-076 admixed with other materials. This fraction is then conveniently chromatographed in order to separate the active C-076 compounds from other material and also to separate and isolate the individual C-076 compounds. The chromatographic techniques which may be employed to purify the C-076 compounds are generally known to those skilled in this art. Examples of such techniques are column chromatography, using such media as silica gel, aluminum oxide, dextran gels and the like, and elution of such columns with various solvents, and/or a combination of two or more solvents, in varying ratios. Liquid chromatography is employed for the detection of the C-076 comounds, and high pressure liquid chromatography may be employed to isolate purified fractions containing one or more of such compounds. Likewise, thin layer chromatography may be employed to detect the presence of, and to isolate the individual C-076 compounds. The use of the foregoing techniques as well as others known to those skilled in this art, will afford purified compositions comprising the C-076 compounds as well as the individual C-076 compounds themselves. The presence of the active C-076 compounds is determined by analyzing the various chromatographic fractions for antiparasitic activity and also by the spectral characteristics (such as ultraviolet and infrared) of said compounds as described below.

The spectral and other physical-chemical characteristics of the individual C-076 compounds are set forth in tabular form in Table I. These compounds are very soluble in most common organic solvents, and are of minimal solubility in water.

The ultraviolet spectral data in Table I were obtained on a Cary Model 15 Ultraviolet Spectrometer in methanol solutions in 1 cm. quartz cells. The concentration of the compound was approximately 25 μg/ml. The ultraviolet absorption, while represented as that of a particular "a series" compound, is actually the absorption of the "a series" compound which contains a minor amount of a "b series" compound. The "a" and "b" series differ only by a —$CH_2$-moiety in a loweralkyl substituent which difference is not associated with the chromophore. Ultraviolet absorption primarily charac- terizes the degree and nature of unsaturation present in the particular compound. The optical rotations were determined using standard techniques with a Karl Zeiss polarimeter. The concentration factor (c) is given as a percent of the compound in the stated solvent.

TABLE I

| | A1a | A1b | A2a | A2b | B1a | B1b | B2a | B2b |
|---|---|---|---|---|---|---|---|---|
| Molecular Formula | $C_{49}H_{74}O_{14}$ | $C_{48}H_{72}O_{14}$ | $C_{49}H_{76}O_{15}$ | $C_{48}H_{74}O_{15}$ | $C_{48}H_{72}O_{14}$ | $C_{47}H_{70}O_{14}$ | $C_{48}H_{74}O_{15}$ | $C_{47}H_{72}O_{15}$ |
| Optical Rotation $[\alpha]_D^{27}$ (CHCl$_3$) | +68.5° ± 2° (C = 0.77) | | +48.8° ± 2° (C = 1.64) | | +55.7° ± 2° (C = 1.06) | | +38.3° ± 2° (C = 0.87) | |
| Molecular Weight (Determined by mass spectrometry). | 886 | 872 | 904 | 890 | 872 | 858 | 890 | 876 |
| Ultraviolet Absorption Spectrum λ-max(mμ) (ε; logε) | 237 (28,700; 4.458) 243 (31,275; 4.495) 252 (20,290; 4.307) | | 237 (28,800; 4.459) 243 (31,740; 4.501) 252 (20,425; 4.310) | | 237 (29,120; 4.464) 243 (31,850; 4.503) 252 (20,510; 4.431) | | 237 (27,580; 4.441) 243 (30,590; 4.486) 252 (20,060; 4.302) | |

13C nuclear magnetic resonance spectral data for C-076 A1a, A2a, B1a and B2a are set forth in Table II below. The spectra are obtained from a Varian Nuclear Magnetic Spectrometer Model CFT-20 in deuterated chloroform solution using tetramethylsilane as an internal standard. The solution volume and the concentration of sample are given for each case, followed by the chemical shifts relative to tetramethyl silane for each compound given in parts per million (ppm). The chemical shifts are given for a single carbon atom unless otherwise indicated in a parenthetical expression following the chemical shift.

TABLE II

| A1 (0.6 ml. 16%) |
|---|
| 12.0, 13.0, 15.1, 16.4, 17.7, 18.4, 19.9, 20.3, 27.5, 30.6, 34.3 (3C), 35.2, 36.6, 39.7, 40.5, 45.7, 56.4 (2C), 57.7, 67.3, 68.2 (2C), 68.4 (2C), 74.9, 76.1, 77.0, 77.5, 78.3, 79.4, 80.6 (2C), 82.0, 95.0, 95.8, 98.5, 118.4 (2C), 119.7, 124.9, 127.8, 135.2, 136.0, 136.1, 137.6, 139.9, 173.8. |

| A2 (0.6 ml. 16%) |
|---|
| 11.8, 12.4, 13.8, 15.1, 17.7, 18.4, 19.9, 20.3, 27.3, 34.3 (3C), 35.2, 35.8, 36.5, 39.8, 40.8, 41.2, 45.7, 56.4 (2C), 57.7, 67.3, 67.7, 68.2 (3C), 69.9, 70.8, 76.1, 77.0, 77.6, 78.3, 79.4, 80.6 (2C), 81.8, 94.9, 98.6, 99.7, 117.7, 118.4, 119.7, 124.9, 135.7, 136.1, 137.6, 140.0, 173.7. |

| B1 (0.3 ml. 16%) |
|---|
| 12.0, 12.9, 15.1, 16.4, 17.7, 18.4, 19.9, 20.2, 27.5, 30.6, 34.3 (3C), 35.2, 36.6, 39.8, 40.5, 45.7, 56.4, (2C), 67.3, 67.8, 68.2 (2C), 68.4 (2C), 75.0, 76.1, 78.3, 79.4 (2C), 80.5 (2C), 82.0, 95.0, 95.8, 98.5, 118.1, 118.4, 120.4, 124.8, 127.9, 135.2, 136.2, 137.9 (2C), 139.7, 173.6. |

| B2 (0.6 ml. 16%) |
|---|
| 11.8, 12.4, 13.8, 15.1, 17.7, 18.4, 19.9, 20.2, 27.3, 34.4 (3C), 35.2, 35.8, 36.5, 39.8, 40.8, 41.2, 45.8, 56.4 (2C), 67.3, 67.7 (2C0, 68.3 (3C), 69.9, 70.9, 76.1, 78.3, 79.4 (2C), 80.5 (2C), 81.8, 94.9, 98.6, 99.7, 117.7, 118.0, 120.4, 124.8, 135.7, 138.0 (2C), 139.8, 173.5. |

The characteristic mass spectral peaks of eight C-076 compounds are given in Table III. The first line of Table III represents the mass to charge ratio (m/e) of the molecular ion of each respective compound, and the remaining numbers record the mass to charge ratio of the principal fragments of each compound. Mass to charge ratios found on the same horizontal row indicate analagous fragments in each compound. The mass to charge ratios which are given as whole numbers were obtained from an LKB Mass Spectrometer Model LKB-9000. The mass to charge ratios which are given to the fourth decimal place were obtained from a High Resolution Varian Mass Spectrometer Model MAT-731.

TABLE III

| A1a | A1b | A2a | A2b | B1a | B1b | B2a | B2b |
|---|---|---|---|---|---|---|---|
| 886.5072 | 872 | 904 | 890 | 872 | 858 | 890 | 876 |
| 742.4229 | 728 | 760 | 746 | 728 | 714 | 746 | 732 |
| 580.3406 | 566.3265 | 598 | 584 | 566 | 552 | 584 | 570 |
| 548.3136 | 534 | 566 | 552 | 548.3131 | 534 | 566 | 552 |
| 456.2886 | 442 | 456 | 442 | 456 | 442 | 456 | 442 |
| 305.2120 | 291.1962 | 323.2225 | 309.2070 | 305 | 291 | 323 | 309 |
|  |  | 305 | 291 |  |  | 305 | 291 |
| 275.1292 | 275 | 275 | 275 | 261.1139 | 261 | 261 | 261 |
| 257.1382 | 257 | 257 | 257 | 257 | 257 | 257 | 257 |
| 221.1527 | 207 | 239.1637 | 225 | 221 | 207 | 239 | 225 |
| 193.1587 | 179.1429 | 211.1691 | 197.1542 | 193 | 179 | 211 | 197 |
| 199.1101 | 199 | 199 | 199 | 199 | 199 | 199 | 199 |
| 169.1226 | 155 | 179.1076 | 179 | 169 | 155 | 179 | 179 |
| 145.0867 | 145 | 145 | 145 | 145 | 145 | 145 | 145 |
| 137.0954 | 137 | 137 | 137 | 137 | 137 | 137 | 137 |
| 127.0754 | 127 | 127 | 127 | 127 | 127 | 127 | 127 |
| 113.0604 | 113 | 113 | 113 | 113 | 113 | 113 | 113 |
| 95.0496 | 95 | 95 | 95 | 95 | 95 | 95 | 95 |
| 87.0444 | 87 | 87 | 87 | 87 | 87 | 87 | 87 |

The attached FIGS. 1 to 8 are accurate reproductions of infrared and proton-nuclear magnetic resonance spectra of four of the C-076 compounds. FIGS. 1–4 are infrared spectra for C-076 A1a, A2a, B1a and B2a respectively. FIGS. 5 to 8 are proton-nuclear magnetic spectra for C-076 A1a, A2a, B1a and B2a respectively. The infrared spectra were obtained on a Perkin-Elmer Infrared Spectrometer Model 421 in chloroform solution. The proton-nuclear magnetic resonance spectra were obtained in deuterated chloroform solution in a Varian Nuclear Magnetic Resonance Spectrometer Model HA-100 and the spectra show chemical shifts given in parts per million (ppm) relative to tetramethyl silane as an internal standard.

Based on experimental data, including the studies and measurements described herein, the C-076 compounds are believed to have the following planar structural formula:

wherein R is the α-L-oleandrosyl-α-L-oleandroside of the structure:

and wherein the broken line indicates a single or a double bond; $R_1$ is hydroxy and is present only when said broken line indicates a single bond.

$R_2$ is iso-propyl or sec-butyl; and $R_3$ is methoxy or hydroxy.

In the foregoing structural formula, the individual compounds are as set forth in Table IV.

TABLE IV

|  | $R_1$ | $R_2$ | $R_3$ |
|---|---|---|---|
| A1a | Double bond | sec-butyl | —OCH$_3$ |
| A1b | Double bond | iso-propyl | —OCH$_3$ |
| A2a | —OH | sec-butyl | —OCH$_3$ |
| A2b | —OH | iso-propyl | —OCH$_3$ |
| B1a | Double bond | sec-butyl | —OH |
| B1b | Double bond | iso-propyl | —OH |
| B2a | —OH | sec-butyl | —OH |
| B2b | —OH | iso-propyl | —OH |

As might be expected, the compounds of this invention wherein $R_2$ is butyl (the "a series" of compounds) and the corresponding compound wherein $R_2$ is propyl (the "b series"), act similarly in most recovery procedures such as those involving solvent extraction. In each pair of "a" and "b" compounds the "a" compound is found in greater amount and generally makes up about 85 to 99% of a mixture of the "a" and "b" compounds. The presence of the iso-propyl compounds is verified in the mass spectra of the compounds wherein the mass peaks representing the fragments containing the butyl group have companion peaks with a mass 14 units (or one-CH$_2$ group) lower. In addition, high pressure liquid chromatography has been employed to separate the A1b component from the A1a component, and the mass spectrum of such A1b compound has been verified by high resolution mass spectrometry (see Table III).

The novel compounds of this invention have significant parasiticidal activity as anthelmintics, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The C-076 compounds of this invention have unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas, blowfly, in sheep Lucilia sp., biting insects and such migrating dipterous larvae as Hypoderma sp. in cattle, Gastrophilus in horses, and Cuterebra sp. in rodents.

The instant compounds are also useful against parasites which infect humans. The most common genera of parasites of the gastro-intestinal tract of parasites of man are Ancylostoma, Necator, Ascaris, Strongyloides, Trichinella, Capillaria, Trichuris, and Enterobius. Other medically important genera of parasites which are found in the blood or other tissues and organs outside the gastro-intestinal tract are the filiarial worms such as Wuchereria, Brugia, Onchocerca and Loa, Dracunculus and extra intestinal stages of the intestinal worms Strongyloides and Trichinella. The compounds are also of value against anthropods parasitizing man, biting insects and other dipterous pests causing annoyance to man.

The compounds are also active against household pests such as the cockroach, Blatella sp., clothes moth, Tineola sp., carpet beetle, Attagenus sp. and the housefly *Musca domestica*.

The compounds are also useful against insect pests of stored grains such as Tribolium sp., Tenebrio sp. and of agricultural plants such as spider mites, (Tetranychus sp.), aphids, (Acyrthiosiphon migratory orthopterans such as locusts and immature stages of insects living on plant tissue. The compounds are useful as a nematocide for the control of soil nematodes and plant parasites such as Meloidogyne spp. which may be of importance in agriculture.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or dicalcium phosphate.

Where it is desired to administer the C-076 compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, perferably of the vegetable oil variety such as peanut oil, cotton seed oil and the like. Other parenteral vehicles such as organic preparation using solketal, glycerol, formal and aqueous parenteral formulations are also used. The active C-076 compound or compounds are dissolved or suspended in the parenteral formulation for administration; such formulations generally contain from 0.005 to 5% by weight of the active compound.

Although the antiparasitic agents of this invention find their primary use in the treatment of helminthiasis, they are also useful in the treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally, good results are obtained with our novel compounds by the oral administration of from about 0.001 to 10 mg. per kg. of animal body weight, such total dose being given at one time or in divided doses over a relatively short period of time such as 1–5 days. With the preferred compounds of the invention, excellent control of such parasites is obtained in animals by administering from about 0.025 to 0.5 mg. per kg. of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal edible bean mill feed, soya grits, crushed limestone and the like. The active C-076 compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular C-076 compound employed, the compounds of this invention are usually fed at concentrations of between 0.00001 to 0.002% in the feed in order to achieve the desired antiparasitic result.

In using the compounds of this invention, the individual C-076 components may be isolated and purified and used in that form. Alternatively, mixtures more of the individual C-076 components may be used. It is not necessary to completely separate the various C-076 compounds obtained from the purification of the fermentation broth. Generally, there is obtained a mixture containing two or more of the C-076 compounds, but having other unrelated compounds excluded therefrom, and such mixture may be used for the treatment of parasitic diseases as described herein. Such a mixture generally will contain unequal proportions of the C-076 compounds, however, all of the compounds have substantial activity and the antiparasitic activity of the mixture can be accurately determined. In particular it may not be necessary to separate the "b" components from the related "a" component. Such compounds differ only in the length of the 25 side-chain. Separation of these closely related compounds is generally not practiced since the "b" compound is present only in a very small percent by weight.

In addition, where the C-076 compounds are to be added to an animal's feed, it is possible to utilize the dried mycelial cake from the fermentation broth. The mycelia contain a preponderance of the activity and since the level of the activity of the mycelia can be determined, it can be added directly to the animal's feed.

The compounds of this invention have a broad spectrum of activity against many internal parasites at low dosage levels and in many different animals. At levels of about 2.5 mg. per kg. of animal body weight, concentrated mixtures of C-076 compounds are fully active in sheep against *Haemonchus contortus, Ostertagia circumcincta, Trichostrongylus axei, Trichostrongylus colubriformis,* Cooperia spp., and *Oesophagostomum columbianum.* Similarly in cattle at dosages as low as 0.043 mg./kg. C-076 B2 is fully active against *Ostertagia ostertagi, Trichostrongylus axei, Trichostrongylus colubriformis, Oesophagostomum radiatum* and *Dictyocaulus viviparus.* In addition, a horse infected with bots (*Gastrophilus intestinalis* and *Gastrophilus haemorrhoidalis*), large and small strongyles and Oxyuris was successfully treated with 10 mg./kg. (about 1% active compounds by weight) of a mixed concentrate of C-076 compounds, and a dog infected with the microfilarial stage of heartworm (*Dirofilaria immitis*) was successfully treated with a single oral dose at 10 mg./kg. (about 1% active compounds by weight) of a mixed concentrate of C-076 compounds. In rodents, such as mice, infections of Syphacia, Nematospiroides and Aspiculuris have been successfully treated by the oral administration of the C-076 compounds or of the concentrates obtained from the extraction of the mycelia.

The C-076 compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The anthelmintic activity of C-076 may be determined by orally administering via the feed, a sample of C-076 individual compound, a mixture of C-076 compounds, a concentrated extract, and the like to a mouse which had been infected 3 days earlier with *Nematospiroides dubius.* At 11, 12 and 13 days after the initiation of the medication, the feces of the mouse are examined for *N. dubius* eggs, and on the next day the mouse is sacrificed and the number of worms present in the proximal portion of the small intestine are determined. An active compound is observed when there is a significant reduction of egg and worm counts when compared to infected, unmedicated controls.

The following examples are being provided in order that the instant invention may be more fully understood. Such examples are not to be construed as being limitative of the invention.

EXAMPLE 1

The contents of a lyophilized tube of *Streptomyces avermitilis* MA-4680 is transferred aseptically to a 250 ml. Erlenmeyer flask containing 305 ml. of Medium 1. The inoculated flask is incubated for 3 days at 28° C. on a rotary shaking machine at a speed of 220 RPM in a 2 inch radius circular orbit. At the end of this time, a 250 ml. Erlenmeyer flask containing 50 ml. of Medium 2 is inoculated with a 2 ml. sample from the first flask. This flask is incubated for 3 days at 28° C. on a rotary shaking machine at a speed of 220 RPM in a 2 inch diameter circular orbit. 50 Ml. of the resulting fermentation broth containing C-076 is effective against an *N.dubius* infection in mice.

| Composition of Media | |
| --- | --- |
| Medium 1 | |
| Dextrose | 20 g. |
| Peptone | 5 g. |
| Meat Extract | 5 g. |
| Primary Yeast | 3 g. |
| NaCl | 5 g. |
| $CaCO_3$ (after pH adjustment) | 3 g. |
| Distilled Water | 1000 ml. |
| pH 7.0 | |
| Medium 2 | |
| Tomato Paste | 20 g. |
| Modified Starch (CPC) | 20 g. |
| Primary Yeast | 10 g. |
| $CoCl_2$ $6H_2O$ | 0.005 g. |
| Distilled Water | 1000 ml. |
| pH 7.2–7.4 | |

EXAMPLE 2

A lyophilized tube of *Streptomyces avermitilis* MA-4680 is opened aseptically and the contents suspended in 50 ml. of Medium 1 in a baffled 250 ml. Erlenmeyer flask. This flask is shaken for 3 days at 28° C. on a rotary shaking machine 220 RPM with a 2 inch diameter circular orbit. A 0.2 ml. portion of this seed medium is used to inoculate a Slant of Medium 3. The inoculated slant medium is incubated at 28° C. for 10 days and stored at 4° C. until used to inoculate 4 more slants of Medium 3. These slants are incubated in the dark for 8 days. One of these slants is used to inoculate 3 baffled 250 ml. Erlenmeyer flasks containing 50 ml. of No. 4 Seed Medium. The seed flasks are shaken for 2 days at 27° to 28° C. on a rotary shaking machine at 220 RPM with a 2 inch diameter circular orbit The contents of these flasks are pooled and used to inoculate (5% inoculum) baffled 250 ml. Erlenmeyer flasks containing 40 ml. of various production media. Flasks containing media 2, 5 and 6 are incubated for 4 days at 28° C. on a rotary shaking machine at 220 RPM with a 2 inch diameter circular orbit. The resulting broth containing C-076 is then harvested and tested for anthelmintic activity. In all cases 6.2 ml. of whole broth and the solids obtained from centrifuging 25 ml. of whole broth are fully active against *N.dubius* helminth infections in mice.

| Medium 3 (Slant Medium) | |
| --- | --- |
| Dextrose | 10.0 g. |
| Bacto Asparagine | 0.5 g. |
| $K_2HPO_4$ | 0.5 g. |
| Bacto Agar | 15.0 g. |
| Distilled Water | 1000 ml. |
| pH 7.0 | |
| Medium 4 (Seed Medium) | |
| Soluble Starch | 10.0 g. |
| Ardamine pH | 5.0 g. |
| NZ Amine E | 5.0 g. |
| Beef Extract | 3.0 g. |
| $MgSO_4$ $7H_2O$ | 0.5 g. |
| Cerelose | 1.0 g. |
| $Na_2HPO_4$ | 0.190 g. |
| $KH_2PO_4$ | 0.182 g. |
| $CaCO_3$ | 0.5 g. |
| Distilled Water | 1000 ml. |
| pH 7.0–7.2 | |
| Medium 5 | |
| Tomato Paste | 40.0 g. |
| Oat Flour | 10.0 g. |
| Cerelose | 10.0 g. |
| Corn Steep Liquor | 5.0 g. |
| Trace Element Mix | 10.0 ml. |
| Distilled Water | 1000 ml. |
| pH 6.8 | |
| Trace Element Mix | 1000 mg. |
| $FeSO_4$. $7H_2O$ | 1000 mg. |
| $MnSO_4$. $4H_2O$ | 1000 mg. |
| $CuCl_2$. $2H_2O$ | 25.0 mg. |
| $CaCl_2$ | 100.0 mg. |
| $H_2BO_3$ | 56.0 mg. |
| $(NH_4)_2MoO_4$. $4H_2O$ | 10.0 mg. |
| $ZnSO_4$. $7H_2O$ | 200.0 mg. |
| Distilled Water | 1000 ml. |
| pH | |
| Medium 6 | |
| CPC Industrial Starch Modified (Available from CPC Corp.) | 40.0 g. |
| Distiller's Solubles | 7.0 g. |
| Autolyzed Yeast (Ardamine pH available from Yeast Products Inc. | 5.0 g. |
| $CoCl_2$. $6H_2O$ | 50.0 mg. |
| Distilled Water | 1000 ml. |
| pH 7.3 | |

EXAMPLE 3

A 0.5 × 1.0 cm. loop of one of the four slants of Medium 3 prepared as in Example 2 is used to inoculate a baffled 250 ml. Erlenmeyer flask containing 50 ml. of Seed Medium No. 4. The seed flask is shaken for 1 day at 27° to 28° C. on a rotary shaking machine at 220 RPM with a 2 inch diameter circular orbit. The seed flask is then stored stationary at 4° C. until it is ready to be used. The contents of this flask are then used to inoculate (5% inoculum) 20 unbaffled 250 ml. Erlenmeyer flasks containing 40 ml. of Medium No. 2. After 4 days incubation at 28° C. on a rotary shaking machine at 220 RPM with a 2 inch diameter circular orbit, 19 of the flasks are harvested and pooled. The combined fermentation broths containing C-076 are filtered affording 500 ml. of filtrate and 84 g. of mycelia. 78 G. of mycelia are extracted with 150 ml. of acetone for ½ hour with stirring and the mixture filtered. The filter cake is washed with 50 ml. of acetone and the filtrate and washings are combined and concentrated to 46.5 ml. 30 Ml. of the concentrate is adjusted to pH 4 with dilute hydrochloric acid and extracted 3 times with 30 ml. portions of chloroform. The extracts are dried by filtering through dry Infusorial Earth (Super-Cel) combined and concentrated to dryness in vacuo. The oily residue of C-076 weighing 91.4 mg. is dissolved in chloroform sufficient to make 3 ml. of solution which represents 1% of broth volume. The C-076 obtained in this recovery procedure is fully active against *N.dubius* infections in mice. In addition, the chloroform extraction achieved a 70 fold purification of C-076 from the whole broth.

EXAMPLE 4

A seed culture is prepared by inoculating 50 ml. of Medium 4 in a 250 ml. baffled Erlenmeyer flask with a 0.5 × 1.0 cm. loop from one of the four slants of Medium 3 as prepared in Example 2. The flask is incubated at 28° C. on a rotary shaking machine at 220 RPM with a 2 inch diameter circular orbit for 2 days. The seed culture is used to inoculate a 2 liter Erlenmeyer production flask containing 250 ml. of Medium 2. The inoculum volume is 5.0 ml. (2%). The production flask is incubated at 28° C. on a rotary shaker at 220 RPM for 4 days. At the end of this time the whole broth containing C-076 is harvested. 6 Ml. of this whole broth when tested in a mouse infected with *N.dubius* is found to be fully active.

EXAMPLE 5

Step A

A 250 ml. baffled Erlenmeyer flask containing 50 ml. of Medium 7 is inoculated with a frozen vial of *Streptomyces avermitilis* MA-4680. The flask is incubated at 28° C. on a rotary shaking machine at 160 RPM with a 2 inch diameter circular orbit at 160 RPM for 24 hours.

| Medium 7 | |
|---|---|
| Dextrose | 1 gm. |
| CPC Industrial Starch Modified | 10 gm. |
| Meat Extract | 3 gm. |
| NZ Amine E | 5 gm. |
| Autolyzed Yeast (Ardamine pH) | 5 gm. |
| $MgSO_4 \cdot 7H_2O$ | 0.05 gm. |
| $Na_4HPO_4$ | 0.19 gm. |
| $KH_2PO_4$ | 0.182 gm. |
| CaCO | 0.5 gm. |
| Distilled Water | 1000 ml. |
| pH 7.0–7.2 | |

STEP B

Two 2 liter baffled Erlenmeyer flasks containing 500 ml. each of Medium 7 are inoculated with 10 ml. of the flask contents of Step A. The media are incubated at 28° C. on a rotary shaking machine at 160 RPM with a 2 inch diameter circular orbit for 24 hours.

Step C

To a 756 liter stainless steel fermentor containing 467 liters of Medium 8 is added 1 liter of the whole fermentation media from Step B. The fermentor is stirred at 28° C. at 130 RPM for 96 hours and with aeration at an air flow of 10 cubic feet per minute.

| Medium 8 | |
|---|---|
| Tomato Paste | 20 gm./l |
| Primary Yeast N.F. | 10 gm./l |
| Starch, modified, CPC | 20 gm./l |
| $CoCl_2 \cdot 6H_2O$ | 5 mg./l |
| Polyglycol 2000 | 0.321 ml./l |
| Distilled Water | q.s. |
| pH 7.2–7.4 | |

At the end of this time 15.5 l. of the whole broth is filtered and the mycelia containing C-076 washed with water. The wet mycelia (2,268 g.) are extracted with 3 liters of acetone with stirring. The mixture is filtered and the filtrate concentrated to 1550 ml. and adjusted to pH 4.0 with dilute HCl. This solution is extracted 3 times with equal volumes of chloroform. The chloroform extracts are dried by filtering through dry Infusorial Earth (SuperCel), combined and concentrated to dryness in vacuo. The residual oil of C-076 weighs 5.12 g. 3.3 Mg. is fully active against *N.dubius* in mice.

4.69 G. of this oil is dissolved in 142 ml. of chloroform and chromatographed on a column containing 90 g. of silica gel packed in chloroform. The column is developed with 1400 ml. of chloroform. The column is then eluted with chloroform/ethanol (49:1) collecting 145 cuts of 5 ml. each. Following this the column is eluted with chloroform/ethanol (19:1) collecting fractions 146–226 of 5 ml. each. Fractions 49–72 are combined and evaporated to dryness affording 200 mg. of an oil (A). Fractions 79–184 are likewise combined and evaporated affording 291 mg. of an oil (B). 400 µg of each fraction is fully active against *N.dubius* in mice.

These two fractions (A and B) are analyzed separately on silica gel thin layer chromatographic plates (Quanta/Gram QIF plates, available from Quanta/Gram Inc., Fairfield, N.J.). The plates are developed with chloroform/methanol (19:1). The spots are analyzed for their ultraviolet activity and one spot of each fraction has the characteristic ultraviolet absorption for the C-076 compounds (see Table I). From fraction A, the spot with an Rf of 0.83 and from fraction B the spot with an Rf of 0.57 have such absorption. These spots represent the C-076 A compounds and the C-076 B compounds respectively.

198 Mg. of the oil (A) above is chromatographed on 80 g. of silica gel packed in chloroform, eluting with chloroform/methanol (199:1) until 520 ml. is collected, followed by chloroform/methanol (99:1) collecting fractions of 10 ml. each. The fraction from 630 to 720 ml. affords 30.4 mg.; the fraction from 730 to 950 ml. affords 78.4 mg. and the fraction from 950 to 1040 ml. affords 20 mg. of an oily material. Fractions 1 and 2 containing C-076 A components when tested in mice against *N.dubius* at levels of 1.0, 0.5 and 0.25 mg. are fully active.

EXAMPLE 6

Step A

A 250 ml. baffled Erlenmeyer flask containing 50 ml. of Medium 8 is inoculated with a frozen vial of *Streptomyces avermitilis MA* 4680. The flask is incubated at 28° C. on a rotary shaking machine at 160 RPM with a 2 inch diameter circular orbit for 24 hours.

Step B

A 2 liter baffled Erlenmeyer flask containing 500 ml. of Medium 8 is inoculated with 10 ml. of the flask contents of Step A. The medium is incubated at 28° C. on a rotary shaking machine at 160 RPM with a 2 inch diameter circular orbit for 24 hours.

Step C

To a 189 liter stainless steel fermentor containing 160 liters of Medium 9 is added 500 ml. of inoculum from Step B. The fermentor is incubated at 28° C. with stirring at 150 RPM for 24 hours aerating at a rate of 3 cubic feet per minute.

| Medium 9 | |
|---|---|
| Dextrose | 1 gm./l |
| Corn Starch | 10 gm./l |
| Meat Extract | 3 gm./l |
| Autolyzed Yeast (Ardamine pH) | 5 gm./l |
| $MgSO_4 \cdot 7H_2O$ | 0.05 gm./l |
| $Na_2HPO_4$ | 0.10 gm./l |
| $KH_2PO_4$ | 0.182 g./l |
| $CaCO_3$ | 0.5 gm./l |
| Distilled Water | q.s. |
| pH 7.0–7.2 | |

Step D

To a 756 liter stainless steel fermentor containing 467 liters of Medium 6 is added 43 liters of inoculum from Step C. The fermentor is incubated at 28° C. with stirring at 130 RPM for 144 hours and with aeration at an air flow rate of 10 cubic feet per minute.

Step E

At the end of this time, the whole broth is filtered and the filter cake containing C-076 is washed with water. The filter cake is slurried in 120 liters of acetone for 30 minutes, filtered and the solids washed with 30 liters of acetone. The acetone washings are combined and evaporated under reduced pressure to a volume of 40 liters. The concentrate is adjusted to pH 4.0 with dilute hydrochloric acid. The concentrate is extracted 3 times with equal volumes of chloroform. The chloroform extracts are dried by filtering through a pad of dry Infusorial Earth (Super-Cel). The extracts are passed through the Super-Cel, then combined. The combined extracts are concentrated under reduced pressure to a volume of 4 liters. The chloroform concentrate is filtered and passed through a column of 2.4 kg. of silica gel in chloroform. The column is eluted with chloroform collecting eight 3.5 liter fractions. The column is then eluted with chloroform/methanol (49:1) collecting eight more 3.5 liter fractions (fractions 9–16). Fraction number 3 is concentrated to dryness affording 76 g. of an oily material containing a preponderance of the C-076 materials.

97% of this material is dissolved in 685 ml. of methylene chloride and chromatographed through 800 g. of silicic acid (Mallinckrodt Chemical Co. 100 mesh seived again through an 80 mesh screen). The column (7.62 cm. diameter, 36 cm. length) is developed with methylene chloride/benzene (7:3), about 7.5 l, followed by 5% isopropanol in methylene chloride/benzene(7:3), 2.25 l. The fraction eluted with the 5% isopropanol in methylene chloride/benzene, which contains a strongly colored band, contains virtually all of the C-076 material, as determined by thin layer chromatography (as described in Example 5). This fraction (500 ml.) is evaporated and rechromatographed on 105 g. of silicic acid (column 3.7 cm. diameter, 18 cm. length) in methylene chloride. The column is developed with 100 ml. portions of methylene chloride containing 5, 10 and 20% ether. Further elution with 20% ether in methylene chloride produces 2 colored bands. The fractions between the two bands contained virtually all of the C-076 material as determined by thin layer chromatography.

The C-076 containing fraction is chromatographed on 59 g. of silicic acid (column 3.7 cm. diameter, 11 cm. length) in methylene chloride. The column is developed with 10% ether in methylene chloride. After the first material begins to elute, a fraction of 70 ml. is taken followed by 26 fractions of 5–6 ml. each. Fractions 3–26 are combined, affording 1.35 g. of material, and analyzed by thin layer chromatography (silica gel plates-Analtech GF 254, developed with 5% isopropanol in methylene chloride). The material with an Rf of 0.28 in this system is C-076 A1.

The column is then eluted with 20% ether in methylene chloride (200 ml.) followed by 50% ether in methylene chloride (800 ml.). A small amount of C-076 A1/A2 mixture is eluted followed by all C-076 A2. The total residue of the C-076 A2 fraction is 800 mg.

Further elution with 5% isopropanol in methylene chloride affords C-076 B1 (135 mg.). The separation is followed by observing the ultraviolet absorption of the eluent. C-076 B1 and A2 have very similar Rf values on silica gel thin layer chromatography plates (Analtech GF 254) in 5% isopropanol in methylene chloride. However, the two components are clearly distinguishable on the same plates developed with 15% isopropanol in hexane.

Figure 1:
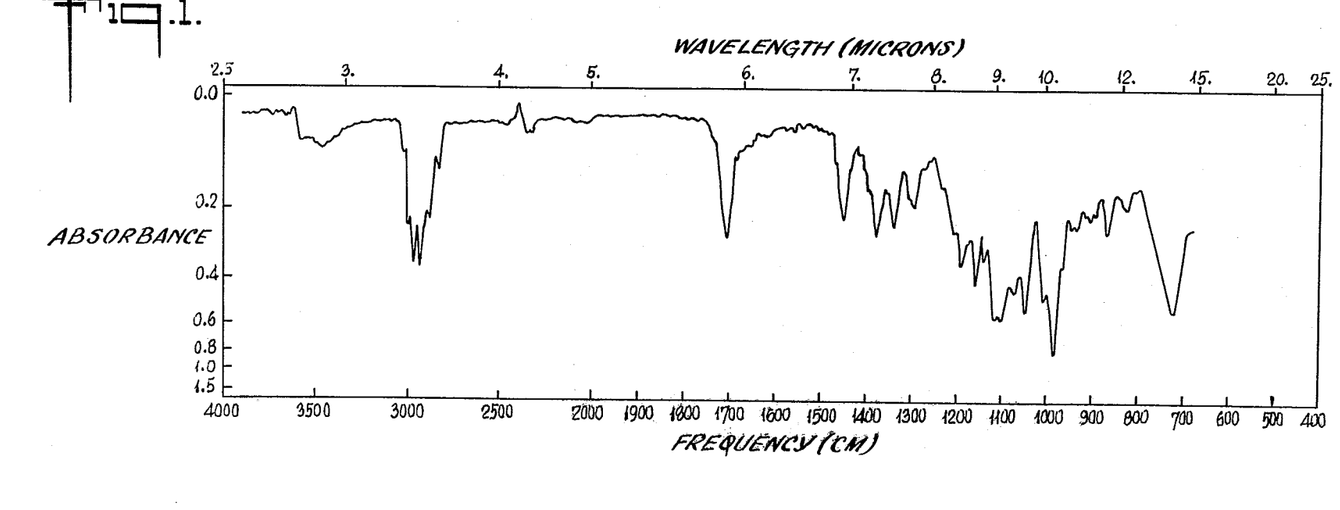
Figure 5:
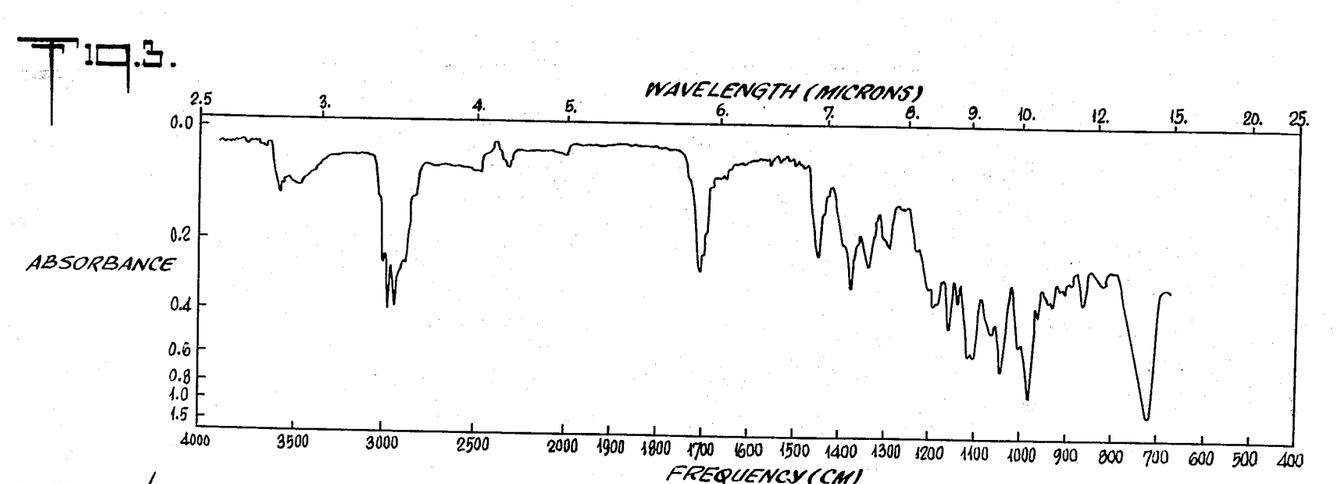

The entire C-076 A1 fraction is applied to 14 silica gel plates (Analtech HF 254, 20×20 cm. 500μ thick). The plates are developed in 10% isopropanol in hexane. The band containing the C-076 A1 is removed from the plates, extracted with ether, evaporated and reapplied to 6 more plates and developed 5 times with 5% isopropanol in hexane. The C-076 A1 is removed from the plates and again chromatographed, developing with pure ether affording 270 mg. of substantially pure C-076 A1. The infrared and nuclear magnetic resonance spectra for this sample are reproduced as FIGS. 1 and 5 and Table II respectively.

Figure 2:
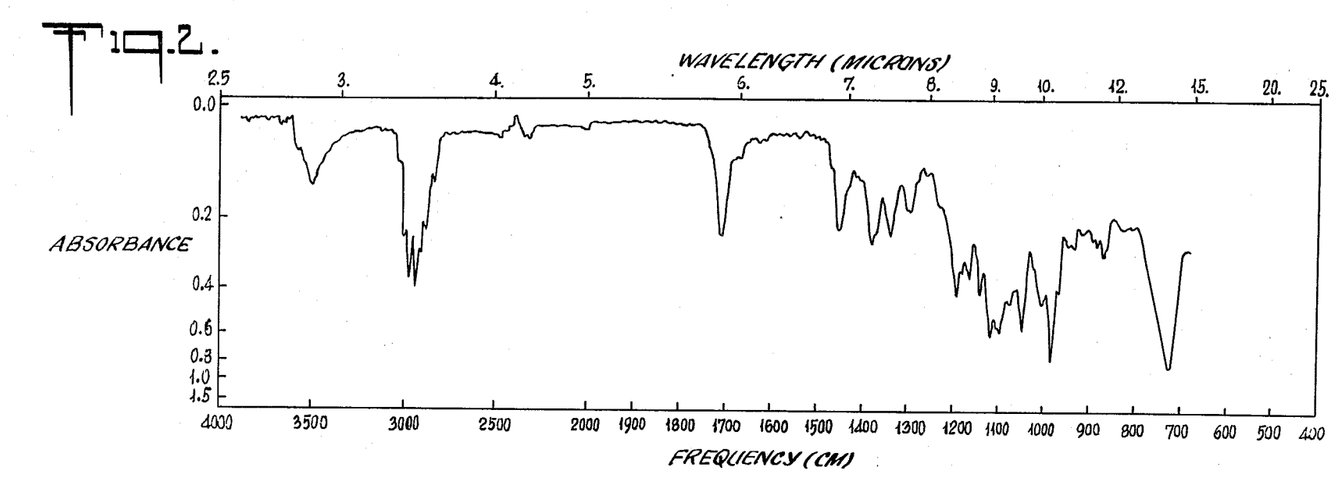
Figures 5, 6:
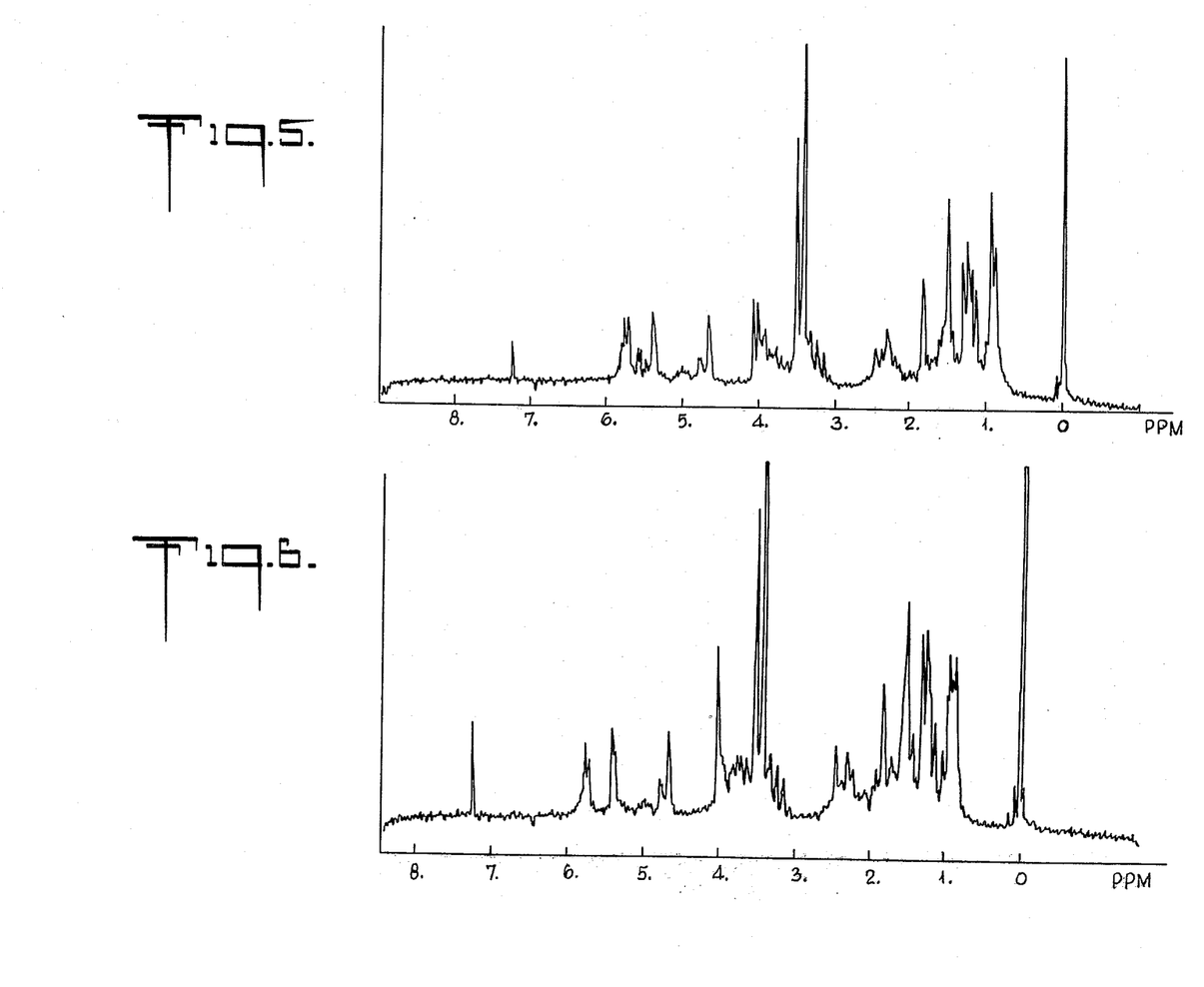

The C-076 A2 fraction is chromatographed on 10 silica gel (Analtech HF 254) plates, developing 5 times with 15% isopropanol in hexane affording 265 mg. of substantially pure C-076 A2. The infrared and nuclear magnetic resonance spectra for this samle are reproduced in FIGS. 2 and 6 respectively, and Table II.

Figure 7:
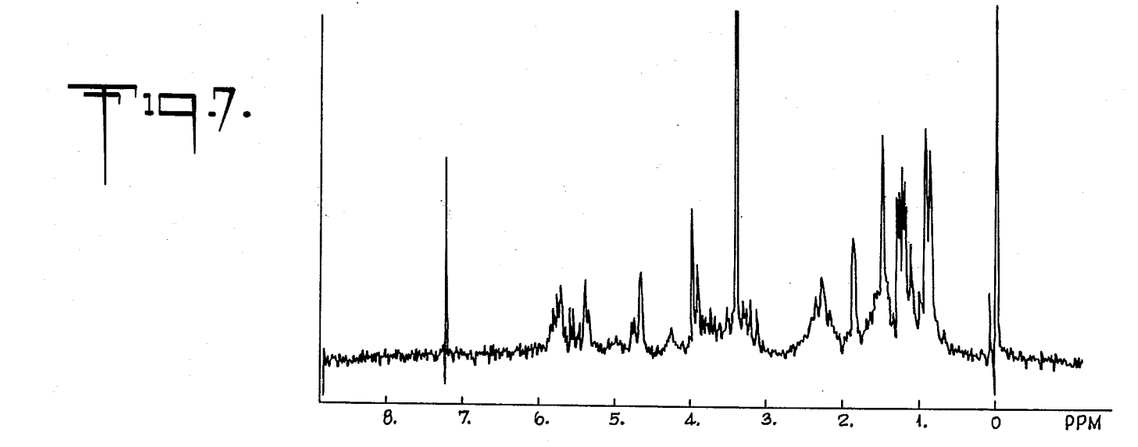

The C-076 B1 fraction is chromatographed on 2 plates (as above) in 15% isopropanol in hexane affording 55 mg. of substantially pure C-076 B1. The nuclear magnetic resonance spectrum of this sample is reproduced in FIG. 7, and Table II.

EXAMPLE 7

The fermentation described in Example 6 is repeated twice and the whole broths are combined. The fermentation broth is work up as described in Example 6 recovering 3.3 l of an initial chloroform extract which contains 60 mg./ml. of total solids and is estimated to be 0.5% C-076 by thin layer chromatographic analysis.

3 Liters of this chloroform solution is chromatographed on 2400 g. of silica gel (Davidson Grade 62) packed in chloroform. The column (9.5×122 cm.) is developed with eight 3800 ml. portions of chloroform (fractions 1–8) followed by eight 3800 ml. portions of chloroform/methanol (49:1 fractions 9–16). The individual fractions are analyzed by thin layer chromatography (silica gel plates, Quanta/Gram QIF) developed with chloroform/methanol 19:1. Fractions 9–11, 12–13 and 14 are each evaporated to dryness affording 6.63 g. of solids containing the C-076 A components in fractions 9–11, 24.91 g. of solids containing C-076 B components in fractions 12–13, and 4.71 g. of solids also containing the C-076 B components in fraction 14.

The material from fractions 12–14 are combined (29.62 g.), dissolved in 100 ml. of methylene chloride and chromatographed on 400 g. of silica gel (Davidson Grade 62) in methylene chloride. The column is eluted with 1500 ml. of methylene chloride/2-propanol (99:1); 1500 ml. of methylene chloride/2-propanol (49:1); 2000 ml. of methylene chloride/2-propanol (19:1); and 1000 ml. of methylene chloride/2-propanol (9:1). The eluent volumes between 5500–6000 ml. (2.56 g.) and 6000–6500 ml. (5.03 g.) are combined in 25 ml. of methylene chloride and chromatographed on 60 g. of silica gel in hexane. A forerun of 70 ml. of hexane and 100 ml. of hexane/diethyl ether (4:1) are taken and the column then developed with 600 ml. of hexane/diethyl ether (1:4) taking 200 ml. cuts, and finally eluting with 700 ml. of ether taking 100 ml. cuts. Column eluent volumes from 400 to 600 ml. affords 2.035 g. of solids containing C-076 B1 components; volumes 600–1100 contained 0.881 g. of solids containing mixed C-076 B1/B2 components; and volumes 1100–1500 ml. contained 0.381 g. of solids containing C-076 B2 components.

The mixed C-076 B1/B2 components are then dissolved in 4.2 ml. of methyl alcohol/water (4:1) and chromatographed on C18 Porasil (Bondapak-37-75 micron size) in the same solvent. The reverse phase high pressure column (more polar components eluted first) is 1.2 meters by 16 mm. and is eluted at a rate of 800 ml. per hour taking 21.3 ml. fractions. The presence of C-076 components is monitored by observing the ultraviolet absorption of the fractions. C-076 B2 is recovered in fractions 24 to 37 and C-076 B1 is recovered in fractions 51–70 recovering 195.4 mg. of C-076 B2 and 137 mg. of C-076 B1.

Each sample is then separately chromatographed on 4 g. columns of silica gel (Davidson Grade 62) in methylene chloride. The columns are eluted with 35 ml. of methylene chloride/methanol (9:1). The last 20 ml. of eluent from each column is collected and evaporated to dryness affording 155.3 mg. of C-076 B2 and 90 mg. of C-076 B1 respectively.

Figure 4:
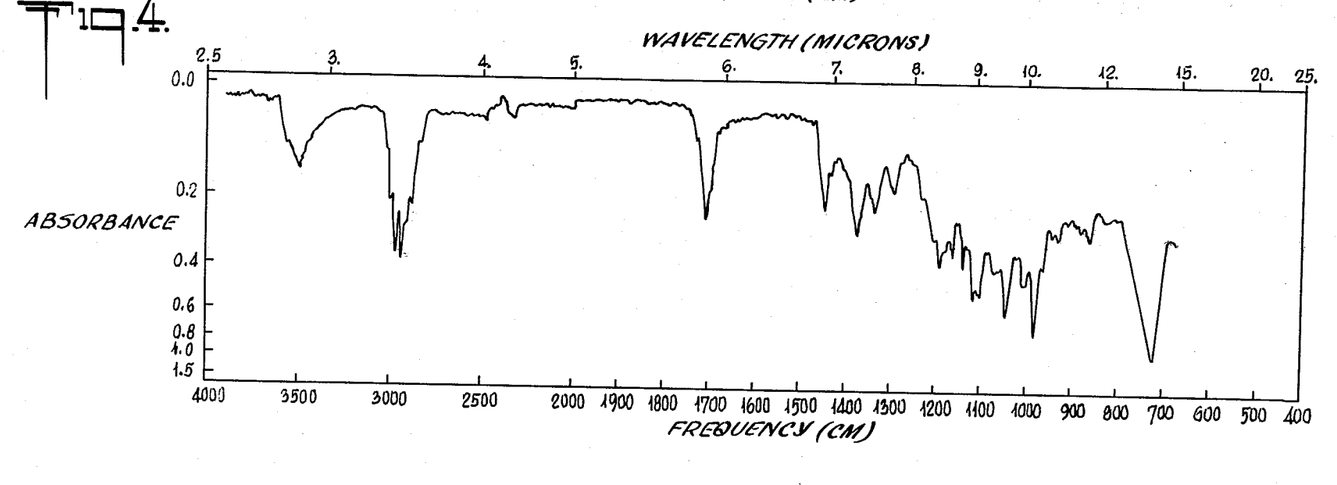
Figure 8:
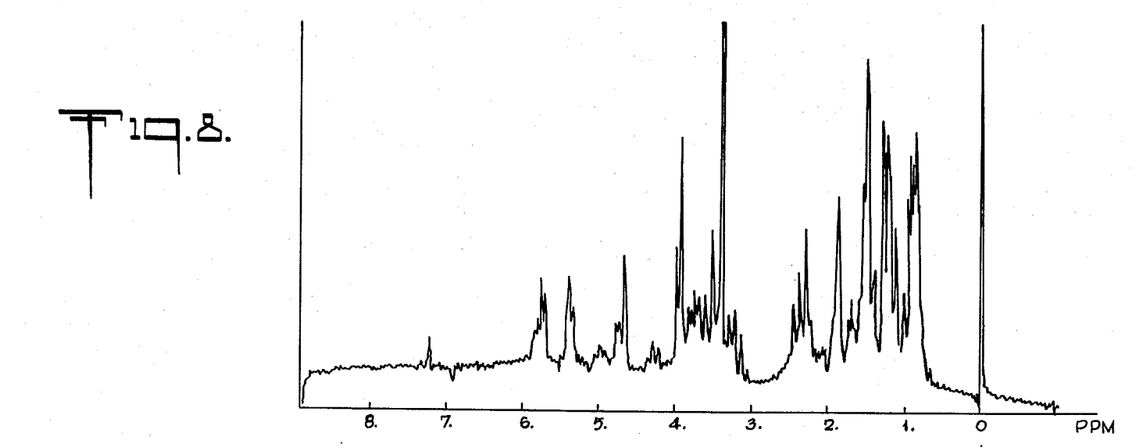

Then 50 mg. of C-076 B1 and 100 mg. of C-076 B2 are chromatographed on preparative silica gel plates (Analtech HF 254), developed with 12% isopropanol in hexane followed by development with ether, recovering C-076 B1 and C-076 B2 which are substantially pure. The infrared absorption spectrum of the thus recovered C-076 B1 and B2 is as shown in FIGS. 3 and 4 respectively. The nuclear magnetic spectrum of the thus recovered C-076 B2 is as shown in FIG. 8.

EXAMPLE 8

A 250 ml. baffled Erlenmeyer flask containing 50 ml. of the following medium:
Lactose: 2.0%
Distiller's solubles: 1.5%
Autolyzed yeast, Ardamine pH: 0.5%
pH—before sterilization: 7.0
is inoculated with the contents of one frozen vial of Streptomyces avermitilis MA 4848 and incubated on a rotary shaker at 28° C. for 24 hours at 150 RPM.

10 Ml. of the above fermentation media is employed to inoculate 500 ml. of the same medium as above in a 2 liter baffled Erlenmeyer flask. The fermentation media is incubated at 150 RPM on a rotary shaker at 28° C. for 24 hours.

All of the foregoing media is employed to inoculate 467 liters of the following media in a 756 liter stainless steel fermentor:
Lactose: 2.0%
Distiller's solubles: 1.5%
Autolyzed yeast, Ardamine pH: 0.5%
Polyglycol 2000: 0.32 ml./liter
pH—before sterilization: 7.0
The fermentation media is incubated at 28° C. for 40 hours with an air flow 10 cubic feet per minute and an agitation rate 130 RPM.

230 Liters of the above media is employed to inoculate 4,310 liters of the following medium in a 5,670 liter stainless steel fermentor:
Dextrose: 4.5%
Peptonized milk: 2.4%
Autolyzed yeast, Ardamine pH: 0.25%
Polyglycol 2000: 2.5 ml./liter
pH—before sterilization: 7.0
The fermentation continues for 144 hours at 26° C. with an air flow rate of 54.3 cubic feet per minute and agitation of 120 RPM.

The fermentation media are filtered and the mycelial filter cake washed with about 550 liters of water, the filtrate and washings are discarded. The filter cake is agitated with about 1500 liters of acetone for about one hour and filtered. The filter cake is washed with a mixture of about 150 liters of acetone and 40 liters of deionized water affording about 2000 liters of extract.

The foregoing fermentation and extraction is repeated on the same scale affording a further 2000 liters of acetone extract which is combined with the first extract and evaporated to a volume of about 800 liters. The pH of the concentrate is adjusted to about 4.7 with concentrated hydrochloric acid and combined with about 800 liters of methylene chloride. The combined solvents are agitated for about 4 hours and separated. The aqueous layer is combined with an additional 800 liters of methylene chloride and agitated for about 4 hours. The layers are separated and each methylene chloride extract separately treated with about 10 kilograms of Super-Cel and filtered. Both extracts are evaporated to a combined volume of about 60 liters.

EXAMPLE 9

The 60 liter solution of C-076 in methylene chloride of the previous example is concentrated to dryness in vacuo and the residue is combined 3 times with 60 liter portions of methanol and evaporated to dryness to remove any residual methylene chloride. The final methanol concentrate volume is approximately 36 liters. The methanol solution is stored overnight and filtered. The filter cake is washed with 40 liters of fresh methanol and the methanol filtrates and washings are combined. The methanol solution is combined with 95 liters of ethylene glycol and 130 liters of heptane. The 2 layer solution is agitated for 5 minutes and the lower layer (ethylene glycol and methanol) is separated. The heptane solution is washed with a mixture of 20 liters of ethylene glycol and 6.3 liters methanol. After five minutes of agitation, the lower layer is separated and combined with the first ethylene glycol/methanol extract. An equal volume of water (approximately 150 liters) containing 79 g. of salt per liter is added to the ethylene glycol/methanol extracts. This solution is extracted with 150 liters of ethyl ether with agitation for 5 minutes. The ether layer is washed with 75 liters of water (½ volume) and agitated for 5 minutes and the layers separated. This procedure is repeated an additional 2 times (the final water was contains 20 g. of salt per liter) affording a final ether layer volume of 110 liters. The ether layer is concentrated in vacuo, to a minimum volume, keeping the temperature less than 25° C. 40 Liters of methylene chloride is added to the residue and the solution is evaporated to dryness. This procedure is repeated and the final residue concentrated in vacuo at 50° C. to dryness.

EXAMPLE 10

A 30 centimeter diameter column is prepared with a layer of 34 kilograms of activated alumina followed by a layer of 34 kilograms of activated carbon in a solution of methylene chloride. The residue from the previous example is dissolved in methylene chloride to a volume of 34 liters and applied to the column and eluted with 34 liters of methylene chloride. These fractions are discarded. A 3% solution of isopropanol and methylene chloride (20.8 liters of isopropanol and 660 liters of methylene chloride) is applied to the column and eluted in approximately 200 liter fractions. The combined isopropanol and methylene chloride fractions are evaporated in vacuo at a bath temperature of about 60° C. to a volume of about 20 liters. The bath temperature is reduced to about 45° C. and the extract is evaporated to dryness in vacuo. The residue is dissolved in 10 parts methylene chloride, 10 parts hexane and one part methanol to a final volume of 15 liters. This solution is applied directly to the Sephadex LH-20 column of the next example.

EXAMPLE 11

A 30 centimeter diameter column is prepared in methanol with 36 kilograms of Sephadex LH-20 (available from Pharmacia Fine Chemicals, 800 Centennial Avenue, Piscataway, N.J. 08854) and washed with a solvent consisting of 10 parts methylene chloride, 10 parts hexane and one part methanol. One-fourth of the C-076 solution of Example 10 is applied to the column and the column eluted at a rate of 250 ml. per minute. Two 20 liter forecuts are collected and discarded followed by 20 two liter rich cuts (identified as fractions 1–20), followed by a single 20 liter tail cut, which is discarded. Fractions 1–8 are found to contain the C-076 A compounds and fractions 9–20 are found to contain the C-076 B compounds.

EXAMPLE 12

The process of Example 11 is repeated on the same scale three more times and all of the fractions containing the C-076 B components (fractions 9–20) are combined and evaporated to dryness, affording 818 g. of crude mixed C-076 B components. The sample is found to contain 55% C-076 B1 and 39% of C-076 B2. 680.5 G. of this sample is dissolved in 2 liters of methylene chloride and placed in a 22 liter three neck round bottom flask followed by the addition of 13.6 liters of methanol. The methylene chloride is removed by distillation. 13.6 Liters of ethylene glycol is added as the methanol is being distilled under reduced pressure. The rate of distillation is maintained such that the temperature of the solution did not go below 65° C. When the addition of the ethylene glycol is complete, the solution is allowed to cool at 5° C. for sixteen hours. The crystals are filtered and washed with 1 liter of cold ethylene glycol. The crystals are then redissolved in 2 liters of methylene chloride the solution placed in a 22 liter three necked round bottom flask. The procedure described above is repeated twice. The first time 12.5 liters each of methanol and ethylene glycol is employed and the second time 13.6 liters each of methanol and ethylene glycol is employed. The final crystals are washed with 1 liter of cold ethylene glycol and 1 liter of water. The crystals are dissolved in 4 liters of water and dried by filtering through sodium sulfate. The benzene solution is concentrated to a volume of 2 liters and lyophilized affording 241.2 gm. of a white powder consisting of 98% C-076 $B_1$ and 1% of C-076 $B_2$.

The mother liquors (22 liters) from the first two crystallizations above are combined and diluted with 22 liters of water. The aqueous solution is extracted with 60 liters of toluene and again with 15 liters of toluene. The toluene extract is then washed with 48 liters of water. The organic phase is filtered through Super-Cel to remove any residual water and evaporated affording 336 gm. of solid material consisting of 79% C-076 $B_2$ and 16% C-076 $B_1$ compounds.

EXAMPLE 13

In the four Sephadex LH-20 columns of the procedure of Example 11, fractions 1–8 contain the C-076 A compounds and are combined. By HPLC analysis the mixture is found to contain 252 g. of C-076 A2a, 16 g. of A2b, 94 g. of A1a and 24 g. of A1b. The material is dissolved in a solvent system consisting of hexane:toluene:methanol in the proportion of 6:1:1 and applied to the Sephadex LH-20 column of the same dimensions as the one used in Example 11 in the above solvent. Fractions are collected at the rate of 250 ml. per minute and a 20 liter forecut is collected and discarded. Further elution affords 2 additional 20 liter forecuts which are also discarded and 50 four liter rich cuts which contain C-076 A compounds. Fractions 3–8 are found to contain predominately C-076 A1 components (40.2 g. A1a and 6.7 g. A1b), and fractions 29–36 are found to contain C-076 A2 compounds (117.2 g. A2a and 7.35 g. of A2b). Fractions 9–28 contain a mixture of C-076 A1 and A2 compounds.

EXAMPLE 14

A sample of 150 g. of C-076 B1 from Example 12 is dissolved in 3 liters of a solvent mixture of hexane:toluene:methanol in the ratio of 3:1:1. The solution is passed through a column of Sephadex LH-20 (of the same dimensions as the one used in Example 11) in the above solvent taking fractions at the rate of 250 ml. per minutes. After two 20 liter portions of the solvent mixture are collected and discarded, forecut of 10 liters is taken and discarded. Then 30 richcuts of 2 liters each are taken. Fractions 1–13 and 25–30 are discarded Fractions 14–16 are combined and contain 80 g. of predominately C-076 B1a. Fractions 22–24 are combined and contain 6.7 g. of predominately C-076 B1b. Fractions 17–21 contain a mixture of C-076 B1a and B1b.

Fractions 17–21 above are combined and concentrated and passed through a Sephadex LH-20 column with the same solvent system as above. Three 20 liter forecuts are taken and discarded. Richcuts are then taken as follows: 5 cuts of 2 liters each (fractions 1–5); 20 cuts of 1 liter each (fractions 6–25); and 10 cuts of 2 liters each (fractions 26–35). Fractions 1–15 are discarded; fractions 16–21 contain 13.5 g. of C-076 B1a and 0.4 g. of C-076 B1b; fractions 22–26 contain 44 g. of C-076 B1a and 0.13 g. of C-076 B1b; fractions 27–30 contain 10.2 g. of C-076 B1a and 0.8 g. of C-076 B1b.

EXAMPLE 15

A mixture of all 8 C-076 components are chromatographed on a high pressure liquid chromatography column 4 mm.×30 cm. packed with 10 micron $\mu$ Bondapak $C_{18}$ silica gel (available from Waters Associates Inc., Maple Street, Milford, Massachusetts 01757) eluting with 85:15 (v/v) methanol:water at a constant 40° C. At a flow rate of 1.2 ml. per minute all eight compounds are separated and the elution volumes, which under the foregoing constant conditions are characteristic of the individual compounds are as follows:

|  | Elution Volume (Ve) Ml |
| --- | --- |
| C-076 $B_2b$ | 5.90 |
| C-076 $B_2a$ | 6.52 |
| C-076 $A_2b$ | 7.12 |
| C-076 $A_2a$ | 7.88 |
| C-076 $B_1b$ | 8.36 |
| C-076 $B_1a$ | 9.60 |
| C-076 $A_1b$ | 10.24 |
| C-076 $A_1a$ | 11.88 |

The separation of C-076 "b" components from the respective "a" components is accomplished using techniques such as high pressure liquid chromatography. An absolute methanol solution of 30 microliters of a mix- ture of C-076 Ala and Alb, estimated to contain 30 micrograms of C-076 Alb is placed on a 3×250 mm. high pressure liquid chromatography column containing Spherisorb 5 micron ODS (available from Spectra Physics) as packing. The column is eluted with 85:15 methanol-water at a rate of 0.15 ml./min. The elution of the products are followed by observing the ultraviolet absorption of the eluent and collecting the individual components at the outlet of the UV monitor. 30 Micrograms of C-076 Alb is recovered and analyzed in a mass spectrometer. The mass spectrum of this sample is recorded in the second column of Table III.

What is claimed is:

1. A compound having the formula:

wherein R is:

and wherein the broken line indicates a single or a double bond; $R_1$ is hydroxy and is present only when said broken line indicates a single bond;

$R_2$ is iso-propyl or sec-butyl; and $R_3$ is methoxy or hydroxy.

2. The compound of claim 1 wherein the broken line indicates a double bond, $R_2$ is iso-propyl and $R_3$ is methoxy.

3. The compound of claim 1 wherein the broken line indicates a double bond, $R_2$ is iso-propyl and $R_3$ is hydroxy.

4. The compound of claim 1 wherein the broken line indicates a double bond, $R_2$ is sec-butyl and $R_3$ is methoxy.

5. The compound of claim 1 wherein the broken line indicates a double bond, $R_2$ is sec-butyl and $R_3$ is hydroxy.

6. The compound of claim 1 wherein the broken line indicates a single bond, $R_1$ is hydroxy, $R_2$ is iso-propyl and $R_3$ is methoxy.

7. The compound of claim 1 wherein the broken line indicates a single bond, $R_1$ is hydroxy, $R_2$ is iso-propyl and $R_3$ is hydroxy.

8. The compound of claim 1 wherein the broken line indicates a single bond, $R_1$ is hydroxy, $R_2$ is sec-butyl and $R_3$ is methoxy.

9. The compound of claim 1 wherein the broken line indicates a single bond, $R_1$ is hydroxy, $R_2$ is sec-butyl and $R_3$ is hydroxy.

10. A composition useful for the treatment of parasitic diseases which comprises an inert carrier having a pharmaceutically effective amount of one or more of the compounds of claim 1 incorporated therein.

11. The composition of claim 10 which is a solid or liquid unit dosage formulation containing from 0.001 to 0.5% by weight of the active compound.

12. The composition of claim 10 which is a feed supplement containing from 0.0002 to 0.3% by weight of the active compound.

13. The composition of claim 10 which is a feed premix containing from 0.005 to 2.0% by weight of the active compound.

14. The composition of claim 10 which is a parenteral formulation containing from 0.005 to 0.5% by weight of the active compound.

* * * * *